United States Patent [19]
Shimizu et al.

[11] Patent Number: 5,976,096
[45] Date of Patent: Nov. 2, 1999

[54] APPARATUS FOR OPHTHALMOLOGIC EXAMINATION

[75] Inventors: Satoshi Shimizu, Yokohama; Shinya Tanaka, Tokyo, both of Japan

[73] Assignee: Canon Kabushiki Kaisha, Tokyo, Japan

[21] Appl. No.: 08/598,010

[22] Filed: Feb. 7, 1996

[30] Foreign Application Priority Data

Feb. 9, 1995 [JP] Japan ................................. 7-021740

[51] Int. Cl.⁶ .................................................. A61B 5/00
[52] U.S. Cl. ......................... 600/504; 600/479; 600/480
[58] Field of Search ................... 128/645–666; 351/206, 208, 211, 215, 216; 600/504

[56] References Cited

U.S. PATENT DOCUMENTS

| | | | |
|---|---|---|---|
| 4,157,708 | 6/1979 | Imura | 128/666 |
| 4,402,325 | 9/1983 | Sawa | 128/666 |
| 4,951,670 | 8/1990 | Tanaka et al. | 128/648 |
| 4,952,050 | 8/1990 | Aizu et al. | 600/504 |
| 4,991,584 | 2/1991 | Kobayashi et al. | 128/648 |
| 4,995,393 | 2/1991 | Katsurgi et al. | 128/648 |
| 5,031,623 | 7/1991 | Kohayakawa et al. | 128/648 |
| 5,107,851 | 4/1992 | Yano et al. | 128/648 |
| 5,129,400 | 7/1992 | Makino et al. | 600/504 |
| 5,455,644 | 10/1995 | Yazawa et al. | 351/206 |
| 5,640,963 | 6/1997 | Tanaka | 600/504 |

*Primary Examiner*—Robert L. Nasser
*Attorney, Agent, or Firm*—Fitzpatrick, Cella, Harper & Scinto

[57] ABSTRACT

An apparatus for ophthalmologic examination includes an illuminating system for applying measuring light onto a measured area at least including a blood current in the fundus to an eye to be examined, a measuring system for measuring the blood current condition of the funds of the eye from a received light signal obtained by receiving the reflected beam of light of the measuring light on the measured area, a pulsation detecting system for detecting the pulsation of a blood current in the measured area, and a signal processing system for determining a trigger point for a predetermined operation on the basis of the detection by the pulsation detecting system.

26 Claims, 12 Drawing Sheets

MEASURED AREA

PATIENT'S DATA

ID#    1234-5678    EXAMINATION DATE  94/6/20
PATIENT NAME  ◯◯ ◯◯    MALE    29 YEARS
CASE HISTORY    DIABETES  HYPERTENSION

MEASUREMENT CONDITION

MEASURING TIME  $V_m$ = 10sec
THRESHOLD VALUE  $V_{th}$ = 15mm/s

MEASURED VALUE

MEASURING TIME UP TO NOW 4 SECONDS
A NUMBER OF PULSATION UP TO NOW 2 TIMES

PARAMETER PER PULSATION

| PULSATION | MAX | MIN | AV |
|---|---|---|---|
| 1 | 29 | 4 | 18 |
| 2 | 30 | 2 | 16 |
| 3 | - | - | - |

APPARATUS FOR OPHTHALMOLOGIC EXAMINATION

BACKGROUND OF THE INVENTION

1. Field of the Invention

This invention relates to an apparatus for ophthalmologic examination for effecting the measurement of the velocity of blood current in the fundus of an eye.

2. Related Background Art

FIG. 1 of the accompanying drawings shows a prior-art example of an eye fundus blood current meter which is one of apparatuses for ophthalmologic examination and in which a slip lamp generally used for ophthalmologic diagnosis and treatment has been reconstructed. The principle of blood current measurement will hereinafter be described by the use of this prior-art example. An illuminating optical system is disposed on an optical path K1, and a beam of white light from an illuminating light source 1 is reflected by an apertured mirror 2 and illuminates a blood vessel Ev on the fundus Ea of an eye through a slit 3, a lens 4 and a contact lens 5 which offsets the refractive power of the cornea of an eye E to be examined and enables the observation of the fundus Ea of the eye. Also, a measuring laser source 6 emitting an He-Ne laser beam for measurement is disposed on an optical path behind the apertured mirror 2, and the measuring light from the measuring laser source 6 passes through the central opening portion of the apertured mirror 2 and is made coaxial with the beam of light from the illuminating light source 1 and illuminates the fundus Ea of the eye in a spot-like shape through the slit 3, the lens 4 and the contact lens 5.

A beam of light scatteringly reflected by blood corpuscles flowing through the blood vessel Ev and the wall of the blood vessel passes through the objective lenses 7a and 7b of a light receiving optical system for stereoscopic observation disposed on optical paths K2 and K3 forming an angle α' therebetween, is reflected by mirrors 8a, 8b and mirrors 9a, 9b and are observed as the image of the fundus of the eye by an examiner through eyepieces 10a, 10b, and the examiner selects a measured area while looking into the eyepieces 10a, 10b and observing the fundus Ea of the eye.

FIG. 2 shows the image of the fundus of the eye observed by the examiner. When in an area I being illuminated by the illuminating light, the blood vessel Ev to be measured is aligned with a scale SC prepared in advance on the focal planes of the eyepieces 10a, 10b, the measuring light from the measuring laser source 6 and the blood vessel Ev are aligned with each other, and the measured area is determined by a spot light beam PS from the measuring laser source 6. At this time, the beam of reflected light of the measuring light reflected by the fundus Ea of the eye is received by photo-multipliers 12a, 12b through optical fibers 11a, 11b.

These received light signals include a predetermined beat signal component created by a component Doppler-shifted by the blood current flowing through the blood vessel Ev and a component reflected by the stationary wall of the blood vessel interfering with each other, and this beat signal is frequency-analyzed to thereby find the velocity of the blood current in the blood vessel Ev.

FIG. 3 of the accompanying drawings shows an example of the result of the frequency analysis of the received light signals measured by the photo-multipliers 12a, 12b, and the axis of abscissas indicates a frequency Δf and the axis of ordinates indicates the output Δs thereof. The relation among the maximum shift Δfmax of the frequency, the wave number vector κi of the incident beam of light, the wave number vector κs of the received beam of light and the velocity vector v of the blood current can be expressed as $$\Delta fmax = (\kappa s - \kappa i) \cdot V \quad (1)$$

Accordingly, when expression (1) is modified by the use of the maximum shifts Δfmax1 and Δfmax2 of the frequency calculated from the received light signals of the photo-multipliers 12a and 12b, the wavelength λ of the laser beam, the refractive index n of the measured area, the angle a formed by light receiving optical axes k2 and k3 in the eye and the angle β formed by light receiving optical axes k2 and k3 in the eye, the maximum velocity Vmax of the blood current can be expressed as $$Vmax = \{\lambda/(n\alpha)\} \cdot |\Delta fmax1 - \Delta fmax2|/\cos\beta \quad (2)$$

By thus effecting measurement from two directions, the contribution of the measuring light in the direction of incidence thereof is offset and the blood current in any area on the fundus Ea of the eye can be measured.

Also, to measure the true velocity of the blood current from the relation between the line of intersection A between a plane formed by the two light receiving optical paths k2 and k3 and the fundus Ea of the eye and the angle β formed by the line of intersection A and the velocity vector v of the blood current, it is necessary to make this line of intersection A coincident with the velocity vector v, with β=0° in expression (2). Therefore, in the example of the prior art, the entire light receiving optical system is rotated or an image rotator is disposed in the light receiving optical system so that the line of intersection A may be made optically coincident with the velocity vector v.

Blood current measurement data recorded by such an apparatus, according to the prior art, are shown in FIG. 4 of the accompanying drawings. Heretofore, the recording of measurement data has been started simultaneously with measurement start Ts and therefore, the phase of the top of the data has been quite random and the comparison thereof with other data has sometimes been difficult. Also, the end Te of data recording has been set by a measurement time Tm and therefore, in which phase of pulsation the data terminates has not been determined, and there has been the possibility that when parameters such as the average flow velocity, the number of pulsations and the maximum and minimum values per pulsation are to be calculated from recorded data, an error is included, depending on the phase of pulsation.

Also, there has heretofore been no apparatus for appropriately measuring a variation in the amount of blood current with time.

Further, there has been desired an apparatus for displaying the result of the measurement of such a state of blood current so that the examiner can appropriately judge it.

SUMMARY OF THE INVENTION

In view of the above-described example of the prior art, the present invention has as a first object thereof to provide an apparatus which performs an apparatus operation conforming to the pulsation of blood current and enables more appropriate and accurate blood current measurement to be effected.

The present invention has as a second object thereof to provide an apparatus which can appropriately measure any variation with time in the amount of blood current.

The present invention has as a third object thereof to provide an apparatus for displaying the result of the measurement of the state of blood current so that an examiner can synthetically and appropriately judge it.

Other objects of the present invention will become apparent from the following detailed description of some embodiments of the invention.

DESCRIPTION OF THE PREFERRED EMBODIMENTS

Figure 1:
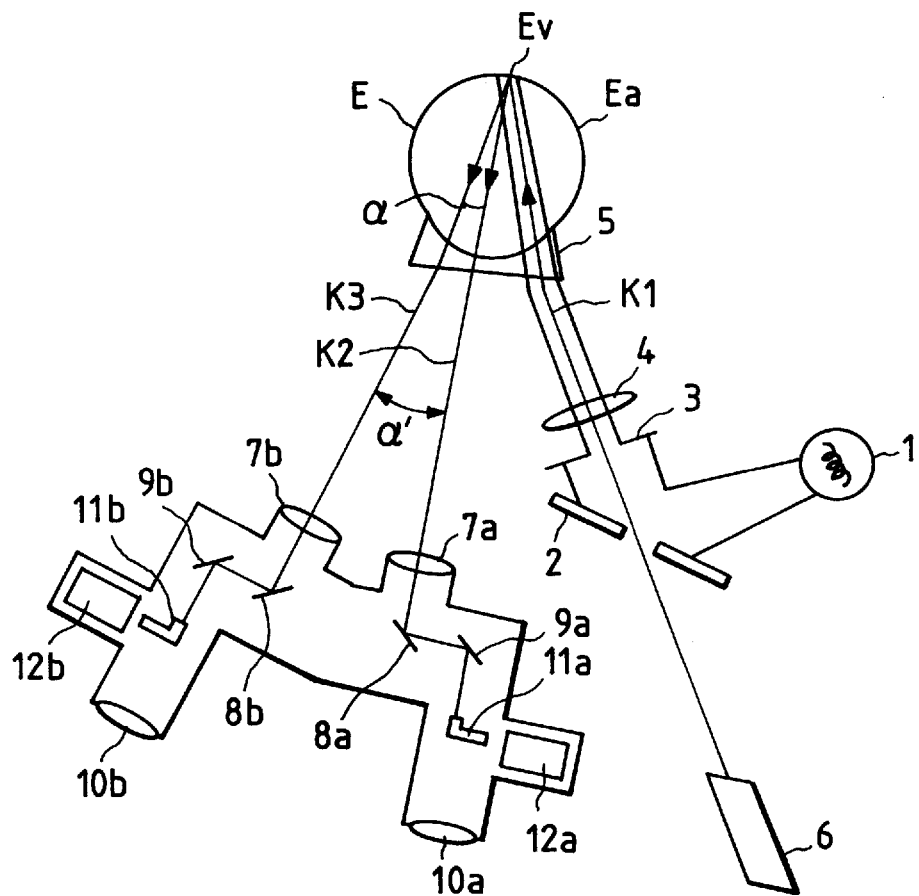
FIG. 1 shows the construction of an eye fundus blood current meter according to the prior art.
Figure 2:
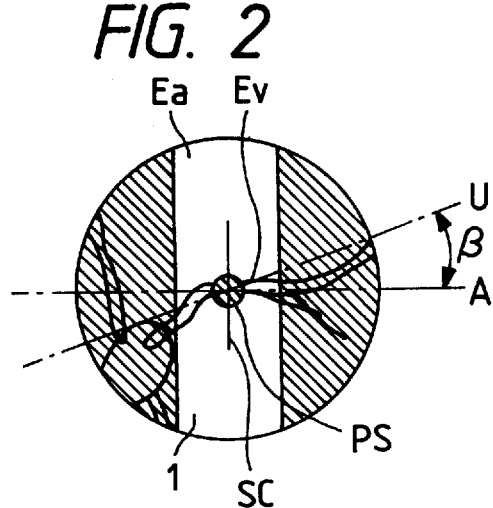
FIG. 2 is an illustration of the image of the fundus of an eye observed.
Figure 3:
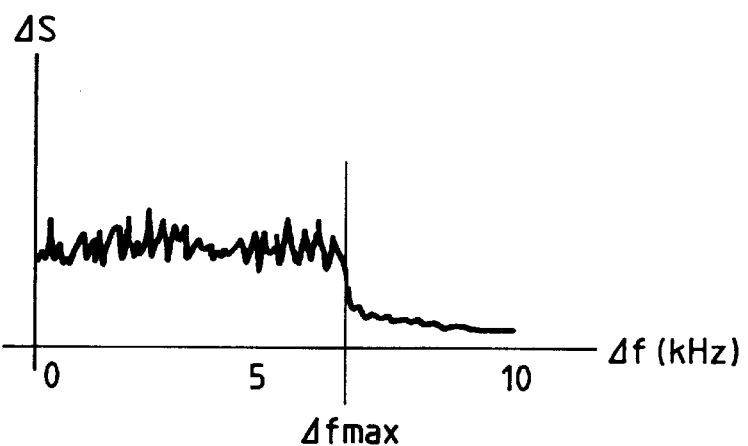
FIG. 3 is a graphical illustration of the frequency distribution of a received light signal.
Figure 4:
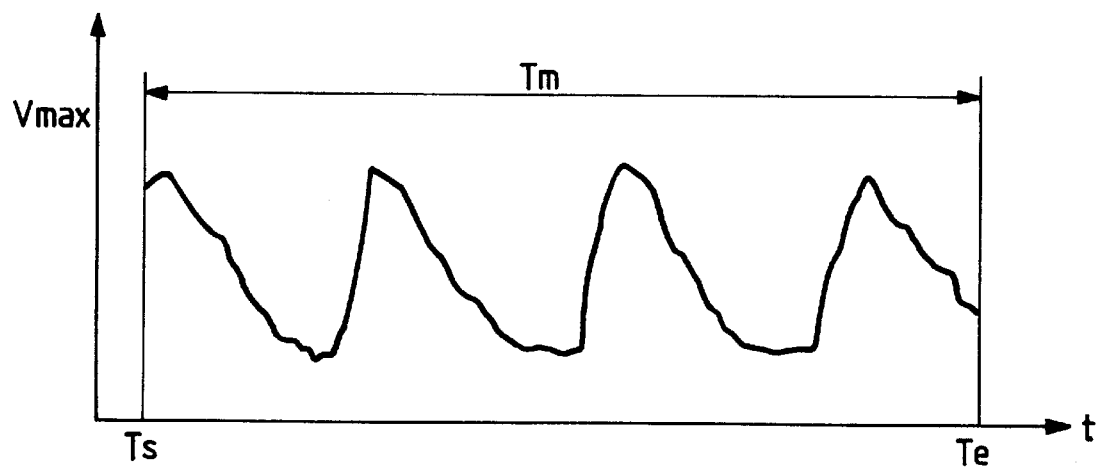
FIG. 4 is a graphical illustration of the measurement data recording by the eye fundus blood current meter according to the prior art.
Figure 5:
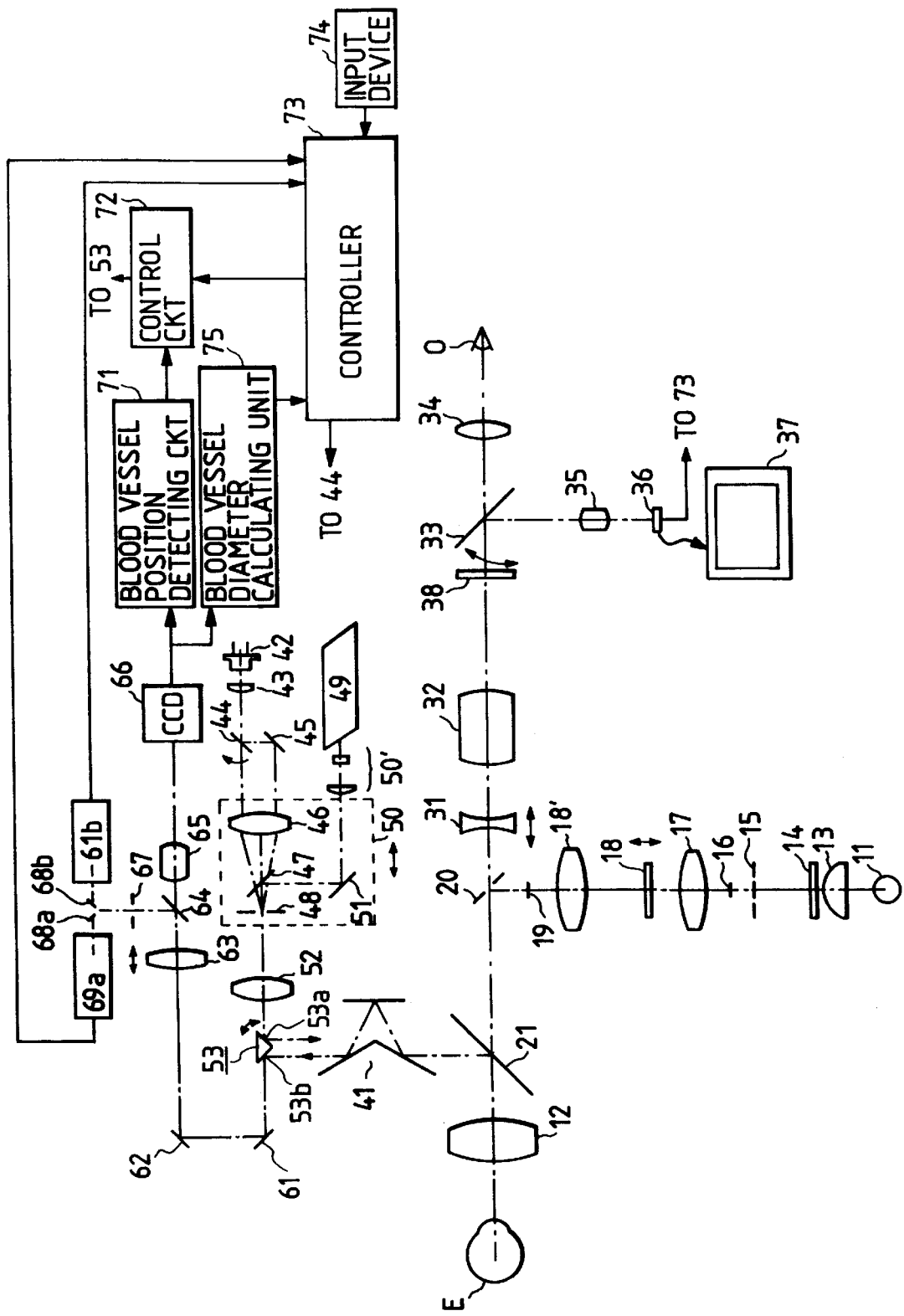
FIG. 5 shows the construction of a first embodiment of the present invention.

FIG. 5 shows the construction of an eye fundus blood current meter according to a first embodiment of the present invention. In FIG. 5, in an illuminating optical path leading from an illuminating light source 11 comprising a tungsten lamp or the like emitting white light to an objective lens 12, there are disposed in succession a condenser lens 13, a band-pass filter 14 transmitting only a beam of light in the yellow range therethrough, a ring slit 15 provided at a location substantially conjugate with the pupil of an eye to be examined, a light intercepting member 16 provided at a location substantially conjugate with the crystalline lens portion of the eye to be examined, a relay lens 17, a transmission type LCD 18 which is an element for fixation target display provided at a location substantially conjugate with the fundus of the eye to be examined, a relay lens 18', a light intercepting member 19 provided conjugately with the vicinity of the cornea of the eye to be examined, an apertured mirror 20 and a band-pass mirror 21 transmitting, for example, a beam of light in the yellow range therethrough and reflecting almost all of the other beams of light.

The fundus of the eye to be examined is substantially uniformly illuminated by the beam of light in the yellow range while a light intercepting area through which illuminating light does not pass to the front eye part of the eye to be examined is formed by the above-described illuminating system. The ring slit and the two light intercepting members are not limited to the present forms, but may be in any form which can form a necessary light intercepting area on the front eye part of the eye to be examined.

The illuminating light, scatteringly reflected by the fundus of the eye, returns to the objective lens 12, is transmitted through the band-pass mirror 21, passes through the opening portion of the apertured mirror 20 and is directed to an observation system of a construction, as will hereinafter be described. At the right of the apertured mirror 20 as viewed in FIG. 5, there are disposed a focusing lens 31, a relay lens 32, a scale plate 38, an optical path switching mirror 33 as optical path switching means, and an eyepiece 34. When the optical path switching mirror 33 is retracted from this optical path, the fundus of the eye E to be examined can be visually observed by an examiner O through the eyepiece 34. At this time, the image of the fundus of the eye is conjugate with the scale plate 38.

When the optical path switching mirror 33 is inserted in the optical path, the image of the fundus of the eye formed on the scale plate 38 is re-imaged and CCD camera 36, which is image pickup means by a TV relay lens 35, and can be displayed and observed on an LCD monitor 37, which is display means. The observation by means of the LCD monitor or the like is useful to mitigate the examiner's fatigue. Also, the output of the CCD camera 36 is connected to a VTR, a video printer or the like, not shown, whereby the recording of the image of the fundus of the eye is possible. This gives birth to the clinical effects that the recording of a measured area is effected and that any change in the region of the fundus of the eye is recorded. Also, the output of the CCD camera 36 is sent to a controller 73, which will be described later, whereby the image of the fundus of the eye can be displayed on the same screen as the graph of the blood current velocity.

On the other hand, the observation by means of the eyepiece 34 is generally higher in resolution and sensitivity than the observation by means of the LCD monitor or the like, and is suitable for reading and diagnosing any fine change in the fundus of the eye. The present embodiment has the advantage that by switching and using these two, an appropriate observation method matching each purpose can be adopted.

A measuring system, which will be described later, is coupled to the reflecting optical path of the bandpass mirror 21 through an image rotator 41. A measuring beam emitted from a laser diode 42 emitting, for example, a red coherent measuring beam, is collimated by a collimator lens 43, whereafter it is reflected by an optical path switching mirror 44 and a fixed mirror 45 and forms a spot at a location conjugate with the fundus of the eye to be examined by a condensing lens 46. It's function will be described later.

On the other hand, a tracking beam emitted from a light source 49 emitting, for example, a green tracking beam of high luminance, is beam-expanded at different vertical and horizontal magnifications by a beam expander 50' comprised of a cylindrical lens, and is reflected by a mirror 51, whereafter it is combined with the measuring beam by a dichroic mirror 47.

The reference numeral 48 designates a tracking beam shaping mask provided at a location conjugate with the fundus of the eye to be examined. The tracking beam shaping mask 48 shapes the tracking beam into an appropriate shape and cuts any unnecessary portion. The spot of the aforedescribed measuring beam is adapted to be positioned at the center of the opening portion of the mask 48. The mask 48, the dichroic mirror 47, the condensing lens 46 and the mirror 51 together form a focus unit 50 and are moved as a unit when the mask 48 is moved so that it may be made conjugate with the fundus of the eye to be examined.

A lens 52 has its front side focus position adjusted to a facet 53a of a micro rotative prism 53 as an optical path deflector disposed at a location substantially conjugate with the pupil of the eye to be examined. The tracking beam and the measuring beam travel toward the image rotator 41 via the lens 52 and the micro rotative prism 53. The two beams having emerged from the image rotator 41 are coupled to the optical axis of the objective lens by the dichroic mirror 21 and are directed to the fundus of the eye to be examined by the objective lens 12. The function of the image rotator 41 at this time will be described later.

The two beams are scatteringly reflected by the fundus of the eye to be examined and are again condensed by the objective lens 12. Thereafter, they are again reflected by the band-pass mirror 21 and are directed to a blood vessel image pickup system and a Doppler light receiving system which will be described later. On the other hand, part of the scattered light of the tracking beam passes through the band-pass mirror 21 as leakage light, passes through the opening portion of the apertured mirror 20 and is directed to the aforementioned observation systems. This scattered light is shaped into the shape of the mask 48 on the fundus of the eye and acts as an indicator indicating a measured area in the observed image of the fundus of the eye.

The beam of light reflected by the band-pass mirror 21 passes through the image rotator 41 and is reflected by a facet 53b of the micro rotative prism 53, whereafter it is reflected by a fixed mirror 61. The micro rotative prism 53 effects the control of the position of the beam entering the eye to be examined on the fundus of the eye to be examined by its facet 53a and effects the control of the received position of the beam of light on the light receiving side by its facet 53b and thus, the two beams of light are position-controlled in their completely separated state and by one and the same control signal. Therefore, the area to which the beams are applied can be received as light/image without fail, and position control, i.e., a tracking control mechanism which will be described later, can be constructed simply. Also, the control of the light applying and light receiving positions is made possible by a single optical path deflecting element (in the present embodiment, the galvanometric mirror) and therefore, the apparatus can be made compact and inexpensive. Further, cross talk between the applied and received beams of light can be greatly mitigated and therefore, an improvement in measurement accuracy also becomes possible.

The scattered light of the tracking beam reflected by the fixed mirror 61, is again deflected by a mirror 62, is transmitted through a focusing lens 63 and a dichroic mirror 64, and by a lens 65, the image of only small part thereof is formed at an enlargement rate greater than that of the observation system on a one-dimensional CCD 66 with an image intensifier, which is a one-dimensional image pickup element. At this time, the illuminating light from the illuminating system does not arrive at the one-dimensional CCD 66 with an image intensifier due to the action of the band-pass mirror 21, but only the image of the fundus of the eye, in the limited area thereof illuminated by the tracking beam, is picked up. Since the spectral reflectances of hemoglobin in blood and melanin on the epidermis of pigment differ most from each other in the green range, the blood vessel to be measured is image-picked up with good contrast by the green tracking beam. Also, the range which is image-picked up, is limited to a narrow range and therefore, it is difficult for any unnecessary flare to mix.

On the other hand, the scattered reflected light of the measuring beam is reflected by the dichroic mirror 64 and has its received area limited by a confocal stop 67 provided at a location conjugate with the fundus of the eye. The action of the confocal stop 67 will be described later. The beam of light transmitted through the confocal stop 67 has only its scattered light in a definite direction extracted by a pair of mirrors 68a and 68b which are light beam selecting means provided substantially conjugately with the pupil of the eye to be examined, and is received independently by photo-multiplier tubes 69a and 69b which are light receiving means.

In FIG. 5, for the convenience of illustration, the pair of mirrors 68a, 68b and the photo-multiplier tubes 69a, 69b are shown as being arranged in the plane of the drawing sheet, but actually they are arranged in a direction perpendicular to the plane of the drawing sheet. Likewise, the optical path of the measuring beam and the optical path from the laser diode 42 to the mask 48 are in a direction perpendicular to the plane of the drawing sheet. Accordingly, the disposition of each beam of light on the pupil of the eye to be examined is as shown in FIG. 6.

Figure 6:
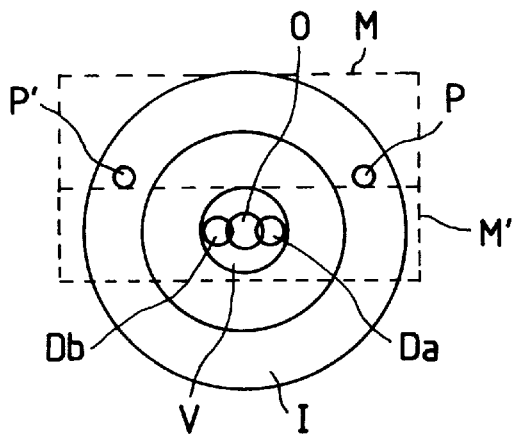
FIG. 6 is an illustration of the disposition of each beam of light on the pupil of an eye to be examined.

In FIG. 6, the letter I designates the image of the ring slit 15, which is a yellow illuminated area on the pupil, the letter O denotes the image of the opening portion of the apertured mirror 20, which is an eye fundus observation light beam area, the letter V designates the image of the effective portion of the facet 53b, which is a light beam area for measurement blood vessel image reception, and the letters Da and Db denote the images of the pair of mirrors 68a and 68b, which are the respective areas of the two beams of light for measurement. The letters P and P' designate the incidence areas of the red measuring beam and indicate the positions of the measuring beam selected by the light beam switching mirror 44 on the pupil.

Also, areas M and M' indicated by broken line is the image of the facets 53a and 53b, respectively. The area M, as shown, is eccentric relative to the optical axis of the objective lens on which the light is incident. The micro rotative prism 53 has a rotary shaft parallel to the lengthwise direction of the mirror on the plane of the drawing sheet of FIG. 6, and by its angle of rotation being adjusted, the measuring position is moved on the fundus of the eye to be examined vertically as viewed in FIG. 6.

Turning back to FIG. 5, the blood vessel image, picked up by the one-dimensional CCD 66 with an image intensifier, is processed into data representative of the amount of deviation of the result from a reference position by a blood vessel position detecting circuit 71, whereafter it is outputted to a control circuit 72, and a control signal for driving the galvanometric mirror 53 is outputted from the control circuit so as to compensate for the amount of movement thereof.

The tracking system constructed as described above, during the operation thereof, performs the tracking operation of holding the measuring beam spot and the image of the confocal stop 67 always on the blood vessel to be measured, and as a result, enables stable measurement independent of the movement of the eyeball to be accomplished. By making the system based on a measurement principle similar to that of the example of the prior art, this tracking can be effected with respect only to a direction orthogonal to the running direction of the blood current in the blood vessel. That is, because of a system whereby the velocity of the blood current is found from the interference signal between the scattered reflected light (reference light component) from the wall of the blood vessel and the scattered reflected component (signal light component) from the blood corpuscles in blood, even if the eyeball moves in a direction parallel to the running direction of the blood current in the eye during measurement, the velocity component corresponding thereto will be offset by the interference between the two and the measured value will be affected in no way.

On the other hand, when the eyeball moves in a direction perpendicular to the running direction of the blood current in the blood vessel, the measuring beam spot and the image of the confocal stop 67 come off the blood vessel and the measured value becomes unstable. The above-described tracking system operates so as to eliminate this.

A signal from an input device 74 for the examiner to actually effect an operating input is inputted to the control circuit 72 through a controller 73 for controlling the entire apparatus, whereby the control of operations, such as the starting and stoppage of the tracking system and the operation of returning the galvanometric mirror 53 to its initial position, is effected.

On the other hand, the outputs of the photo-multiplier tubes 69a and 69b are transmitted to the controller 73, and frequency analysis is effected as in the example of the prior art.

Also, the internal fixation target LCD 18, the focusing lens 31, the focus unit 50 and the focusing lens 63 are interlockingly driven by a single interlocking mechanism, not shown, whereby the image pickup surface of the CCD camera 36, the internal fixation target LCD 18, the mask 48, the image pickup surface of the CCD 66 with an image intensifier, and the confocal stop 67 are always made optically conjugate with one another.

In the apparatus constructed as described above, prior to measurement, the examiner first effects the alignment of the entire apparatus with the eye E to be examined. This operation is similar to that of a popular retinal camera, and the examiner effects the operating input while looking at the eye to be examined through the eyepiece 34 or by the use of the LCD monitor 37.

Figure 7A:
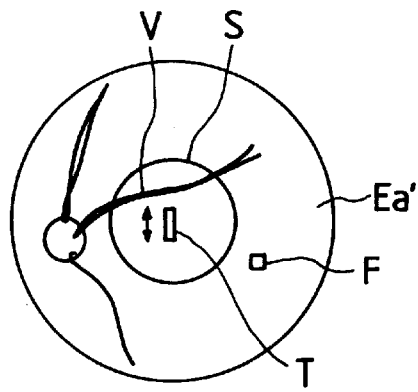
FIGS. 7A to 7C are illustrations of the image of the fundus of the eye observed on a monitor.

When the alignment is completed, the image Eat of the fundus of the eye as shown in FIG. 7A is displayed on the LCD monitor 37. The tracking beam T on the band-pass mirror 21 is displayed as an indicator representative of the measuring position at the center of the LCD monitor.

The examiner first effects the adjustment of focusing so that he can clearly observe the image of the eye to be examined in this state. By the work of the aforedescribed interlocking mechanism, the internal fixation target (LCD) 18, the mask 48, the image pickup surface of the CCD 66 with an image intensifier and the confocal stop 67 are made conjugate with the fundus of the eye to be examined at the time of this operation. In this state, the indicator T becomes the image of the mask 48. In FIG. 7A, the letter F designates a shadow formed by the internal fixation target LCD 18 and is clearly imaged on the fundus of the eye to be examined with the indicator T. The examiner fixates at this shadow F as a fixation target to thereby stabilize his eye. This shadow F can be moved two-dimensionally on the fundus of the eye to be examined on the monitor by the examiner operating an operating member such as a joy stick, not shown, in the input device 74.

The central circle S on the monitor is a scale prepared on the scale plate 38 and indicates the range within which the tracking beam T can be moved by driving the micro rotative prism 53. Also, the direction in which the tracking beam T is moved by the driving of the micro rotative prism 53 is one direction, i.e., the lengthwise direction indicated by an arrow in FIG. 7A.

Figure 7B:
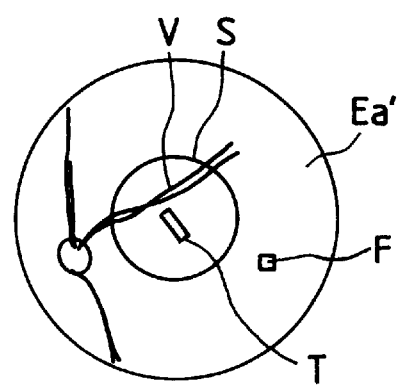

In this state, the examiner operates the input device 74 and moves the fixation target F to thereby guide the blood vessel V to be now measured into the circle S. The examiner then rotates the image rotator 41 so that the tracking beam T may become perpendicular to the running direction of the blood current in the blood vessel V to be measured. At this time, the image rotator 41 is not acting on the observation system and therefore, only the tracking beam T rotates. Also, as a matter of course, the light beam position on the pupil shown in FIG. 6 rotates, and a straight line passing through the centers of beams of light Da and Db for Doppler detection is made coincident with the running direction of the blood vessel V and a straight line passing through the centers of beams of measuring light P and P' is likewise made coincident with the running direction. This corresponds to the fact that $\beta$ in the aforementioned expression (2) is made into 0° (the state of FIG. 7B).

The advantage of adjusting this $\beta$ to 0° will hereinafter be described.

First, when from expression (2), $\beta=90°$, that is, cos $\beta=0$, it becomes impossible to find the absolute value of the maximum blood current velocity Vmax from the maximum frequency shifts $\Delta fmax2$ and $\Delta fmax2$, but if the image Ea' of the fundus of the eye is rotated so that $\beta=0°$, the measurement impossible position can be avoided.

Also, it becomes unnecessary to measure the angle $\beta$ and therefore, the factors of errors decrease and the work is simplified.

Further, as previously described, the velocity of the blood current is found from the interference signal between the scattered reflected light from the wall of the blood vessel and the scattered reflected light in the blood and therefore, even if during measurement, the fundus of the eye moves in the direction of the blood current, the result of the measurement will not be affected thereby.

Figure 7C:
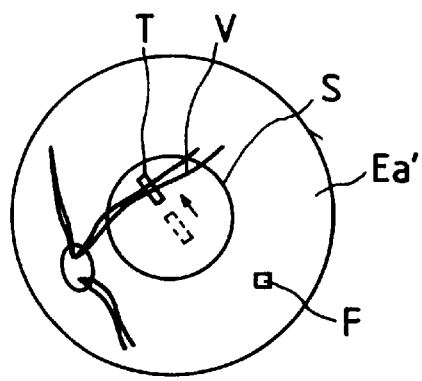

The examiner then operates another operating member, not shown, in the input device 74 to thereby adjust the center of the tracking beam T to the blood vessel V to be measured (the state of FIG. 7C), and operates the input device 74 to thereby command the start of tracking.

The measuring beam is superposed on the central portion of the tracking beam T and that region is the measuring point, as previously described.

The position of the tracking beam T on the CCD 66 at the start of this tracking is stored as the initial position of the micro rotative prism 53 in the control circuit 72 at a point in time at which it has been reported that there has been an operating command from the input device 74 to the control circuit 72 through the controller 73. At this time, the image of this blood vessel is formed substantially on the center of the CCD 66 with an image intensifier. The control circuit 72, when it receives a command for the starting of tracking, starts the drive control of the micro rotative prism 53 on the basis of the data representative of the amount of deviation from the reference position (initial position) outputted from the blood vessel position detecting circuit 71 so that the blood vessel may always be held at the reference position.

When in the state in which the alignment has thus been completed and the tracking has been started, the examiner depresses the measurement switch, not shown, of the input device 74 to start measurement, the signals of the photo-multipliers 69a and 69b are introduced into the controller 73, and the maximum frequency shifts |Δfmax1| and |Δfmax2| by the signal light incident from a position P in FIG. 6 on the pupil of the eye E to be examined are first found. |Δfmax1| is the result of the processing of the output signal from the photo-multiplier 69a and |Δfmax2| is the result of the processing of the output signal from the photo-multiplier 69b.

The inputted signal light is positioned at P and is provided at a position sufficiently eccentric relative to the received light beam positions Da and Db and therefore, usually the maximum velocity Vmax can be found by $\cos\beta=0$ in expression (2) and Vmax=$\{\lambda/(n\alpha)\}\cdot$|Δfmax1−Δfmax2|, but depending on the position of the blood vessel Ev on the fundus of the eye, there is a case where the true flow velocity must be Vmax=$\{\lambda/(n\alpha)\}\cdot$|Δfmax1+Δfmax2|. In the present embodiment, as a tentative measurement, the maximum velocity Vmax by the aforementioned expression (2) is first calculated in this state, whereafter the optical path switching mirror 44 is retracted out of the optical path by the controller 73, and the signal light is made incident from a position P1 on the pupil of the eye to be examined to thereby effect measurement.

The position P' on the pupil, as shown in FIG. 6, is disposed so as to have its center on a straight line passing through the center of the other incidence position P and parallel to a straight line passing through the centers of the received beams of light Da and Db, and particularly in the present embodiment, it is chosen so that the spacing therebetween may be greater than the distance between the centers of the received beams of light Da and Db and a straight line linking the middle points of the two straight lines together may be orthogonal to the straight line passing through the respective centers.

The position of the incident beam of light is changed over from P to the thus disposed P', whereafter the controller 73 introduces signals from the two photo-multipliers 69a and 69b thereinto, calculates respective maximum frequency shifts |Δfmax1'| and |Δmax2'| in accordance with expression (2). The maximum velocity Vmax at this time is Vmax'.

By the incident beam of light being selected as described above, an area in which the actual directions of shift are opposite to each other between the maximum frequency shifts |Δfmax1| and |Δfmax2|, that is, the signs thereof change over therebetween, and an area in which the signs of |Δfmax1'| and |Δfmax2'| change over therebetween, can be separated from each other. That is, however may be set the angle of incidence onto the fundus of the eye, it never happens that both of the signs of |Δfmax1| and |Δfmax2| and the signs of |Δfmax1'| and |Δfmax2'| have changed over.

In an area wherein neither of the signs changes over, Vmax≅Vmax'. Also, in a case where the sign changes over in one of Vmax and Vmax', it is possible to create the relation that in the measured value of the maximum velocity, (the side on which the changeover of the sign does not take place)>(the side on which the changeover of the sign takes place).

Accordingly, in the apparatus of the present embodiment, the controller 73 controls the apparatus so as to compare the two maximum velocities Vmax and Vmax' with each other, determine the direction of incidence of appropriate signal light for finding a true maximum flow velocity, change over the optical path switching mirror 44 to an appropriate direction on the basis of this determination, and effect main measurement thereafter in this direction. For example, when the main measurement is to be effected by the use of expression (2), the direction of the optical path switching mirror 44 is determined so that the main measurement may be effected in the direction of incidence of the beam of light in which the greater measured value of Vmax and Vmax' has been obtained.

In the main measurement, the measurement and calculation of the maximum velocity Vmax (or Vmax') are repeated at such intervals which will be described later, and continuous measurement is effected.

In the present embodiment, there has been shown a method of judging before the main measurement which of the maximum velocities Vmax and Vmax' should be regarded as the true measured value in the main measurement. Instead of this, however, it is also possible to cope with this situation by software which instructs measuring of the maximum velocities Vmax and Vmax' before the main measurement, checking on the presence or absence of the reversal of the sign after the calculation, and setting such a program in which for example, the calculation sign of expression (2) is reversed when the optical path switching mirror 44 has been changed over to the side to which the sign has been reversed by that presence or absence, so that to whichever side the optical path switching mirror is changed over to effect the main measurement, the true measured value may be obtained.

The detection of the blood vessel diameter will now be described.

Figure 8:
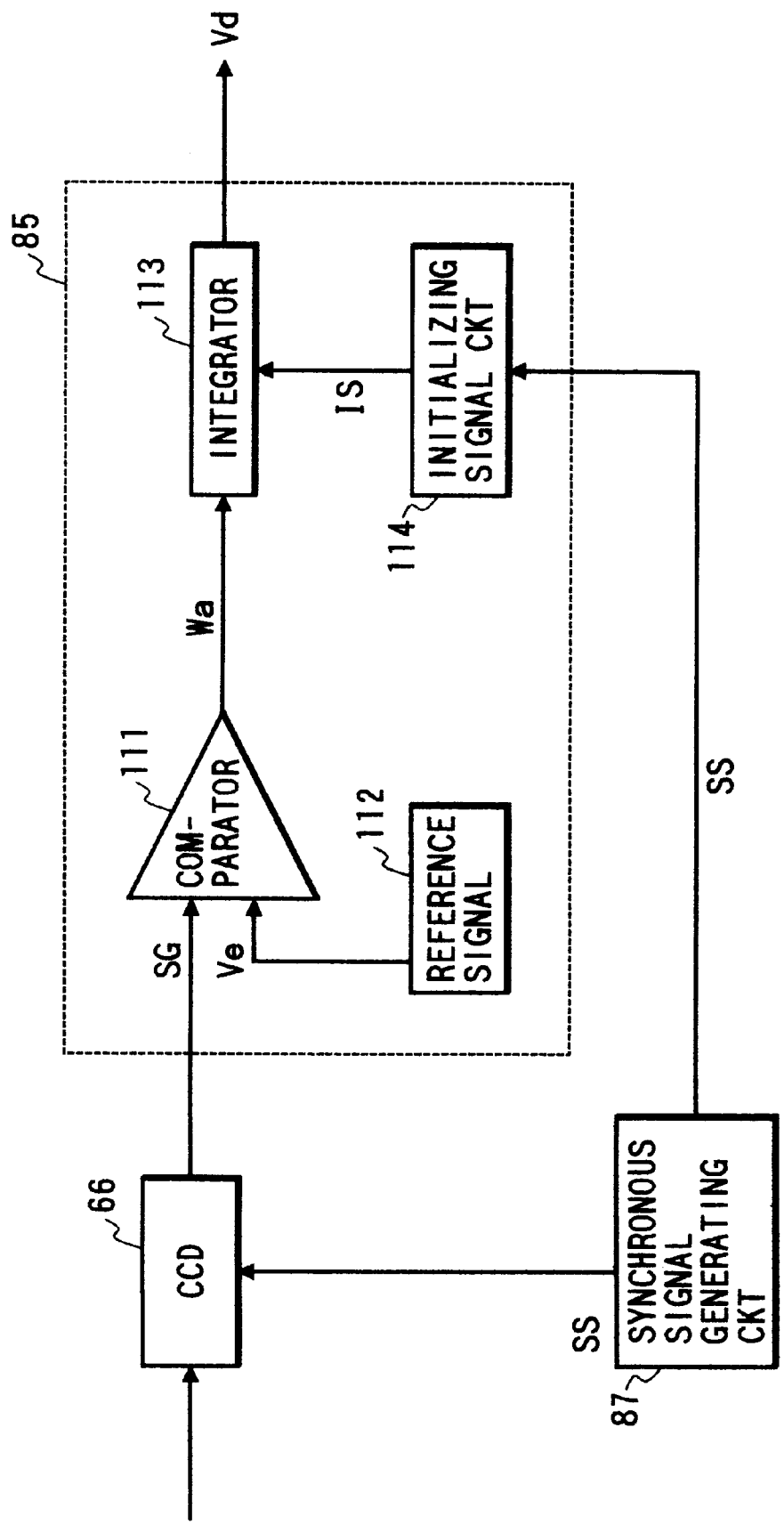
FIG. 8 is a block diagram of a circuit for calculating the diameter of a blood vessel.
Figure 9:
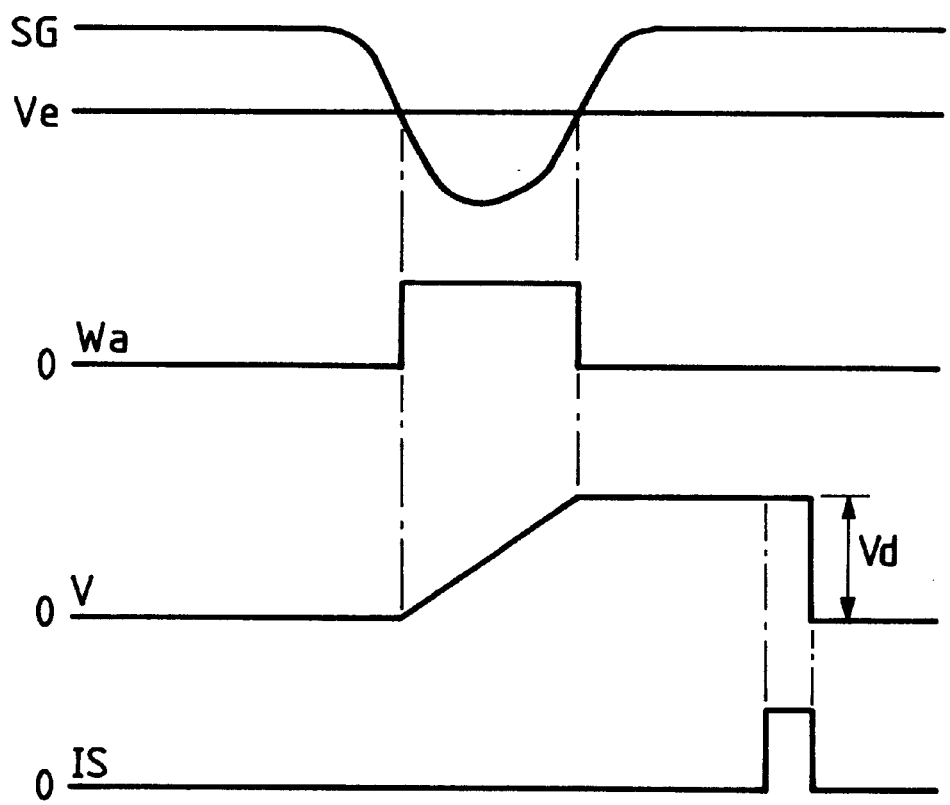
FIG. 9 is a timing chart of the calculation of the diameter of the blood vessel.

FIG. 8 is a block diagram of a blood vessel diameter detecting portion 75, and FIG. 9 shows a timing chart thereof. In FIG. 8, the output SG of the CCD 66 and the reference voltage output Ve of a reference voltage generating circuit 112 are connected to the comparator 111 of the blood vessel diameter detecting portion 75, and the output Wa of the comparator 111 is connected to an integrator 113, which is adapted to output a blood vessel diameter signal. Also, the output IS of an initializing signal circuit 114 is connected to the integrator 113, and the synchronous signal SS of a synchronous signal generating circuit 87 is connected to the initializing signal circuit 114.

In synchronism with the synchronous signal SS from the synchronous signal generating circuit 87, the signal SG from the CCD 66 is inputted to the comparator 111. The comparator 111 compares the predetermined reference voltage Ve from the reference voltage generating circuit 112 and the signal SG with each other, and inputs the output thereof to the integrator 113.

The output Wa of the comparator 111 is integrated by the integrator 113 to thereby obtain a potential V. This potential V is cleared in each cycle of measurement by the signal IS from the initializing signal circuit 114. The output potential Vd of the integrator 113 immediately before being cleared corresponds to the blood vessel diameter.

The blood vessel diameter thus found, like the blood current velocity, is sent to the controller 73. The controller 73 calculates the amount of blood current from the obtained blood current velocity and blood vessel diameter. The blood current velocity, the blood vessel diameter and the amount of blood current are displayed on a display unit, such as a display or a plotter, and it becomes possible to observe the blood vessel diameter, the blood current velocity, and the amount of blood current in real time.

Figure 10:
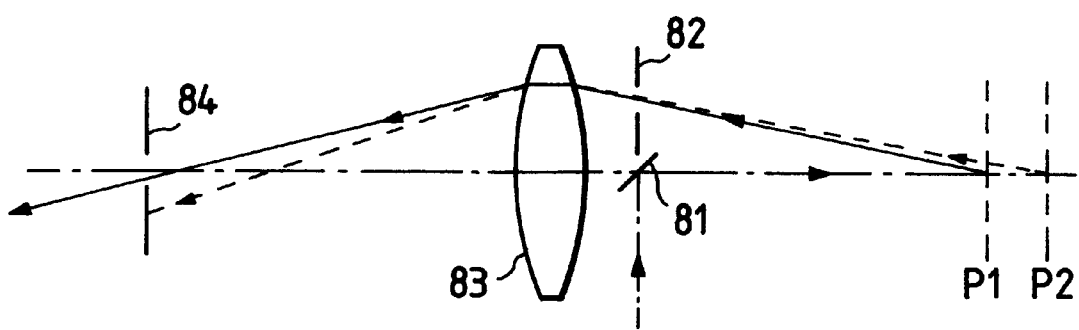
FIG. 10 is an illustration of a confocal stop.

The action of the confocal stop 67 will now be described with reference to FIG. 10, which is a model view. The arrangements of the model view and the actual construction somewhat differ from each other, but are the same in principle.

The position of the blood vessel on the fundus Ea of the eye to be measured is represented by a measured area P1 and further, the position of the blood vessel in the choroid behind this blood vessel is represented by a measured area P2. The beam of light from the measuring laser source 67 is incident on a mirror 81 from below it, is reflected in the left to right direction thereby, and irradiates the measured area P1. The reflected light from the measured area P1 passes through an opening 82 having a function equal to that of one of the pair of small mirrors 68a and 68b, i.e., the function of determining the direction of light reception, is made conjugate with the measured area P1 by a lens 83, and passes through a small hole 84 having a function similar to that of the confocal stop 67, whereafter it is received by a photo-multiplier, not shown. On the other hand, in this optical system, the reflected light from the measured area P2, which is indicated by a dotted line, is imaged by the lens 83 like the beam of light reflected by the measured area P1, which is indicated by a solid line, but it cannot pass through the small hole 84 and therefore is not received by the photo-multiplier.

By the action of such a confocal stop 67, in the present embodiment, it becomes possible to cause only the reflected beam of light in the blood vessel V at a particular depth to be received by the photo-multipliers 69a and 69b, thereby effecting the measurement of the velocity of only a desired blood current. In an actual examination, the examiner effects the setting of the depth of the blood vessel V to be measured by means of a focus knob, not shown, while looking at the focus state on the image Ea' of the fundus of the eye displayed on the monitor 37 shown in FIG. 5, and effects the focusing of the image Ea' of the fundus of the eye. After the completion of the focusing, the examiner effects measurement, makes the blood vessel V and the tracking beam T coincident with each other, and selects a measured area, as previously described.

The recording and display of data will now be described. In the controller 73, the output signals of the photo-multipliers 69a and 69b are read at a rate of 20 points per second, and the value of Vmax is calculated as a digital value. A point which is the trigger during each pulsation it real time is found out by the use of this Vmax, and the timing of the starting and termination of the recording of the data of Vmax is optimized, whereby the recording of the data can be accomplished under a suitable condition. This will hereinafter be described.

Figure 11:
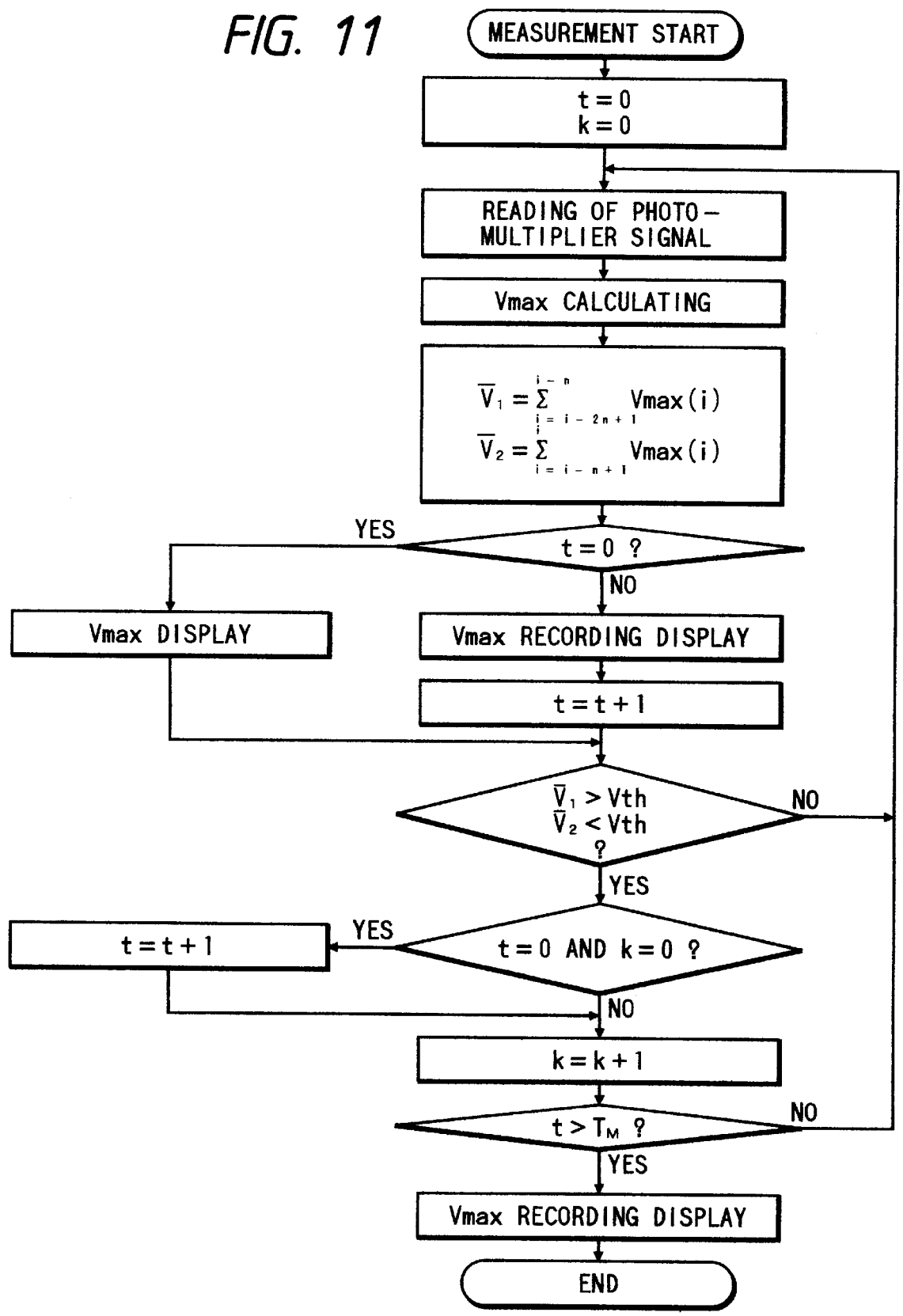
FIG. 11 is a flow chart of measurement data recording.

FIG. 11 shows a flow chart of the recording of the measurement data of the controller 73. When the operator first depresses the measurement starting switch of the input means 74 and a measurement starting signal is sent, a pulsation frequency counter value k and a data recording time counter value t are set to their initial values 0.

Subsequently, the output signals of the photo-multipliers 69a and 69b are read and a blood current velocity Vmax(i) is calculated by the aforedescribed method. The reading of the output signals of the photo-multipliers 69a and 69b each time is effected at every 1/20 second by a clock, not shown, and at the same time, the value of Vmax is plotted on a graph on the monitor in real time by a broken line.

Figure 12:
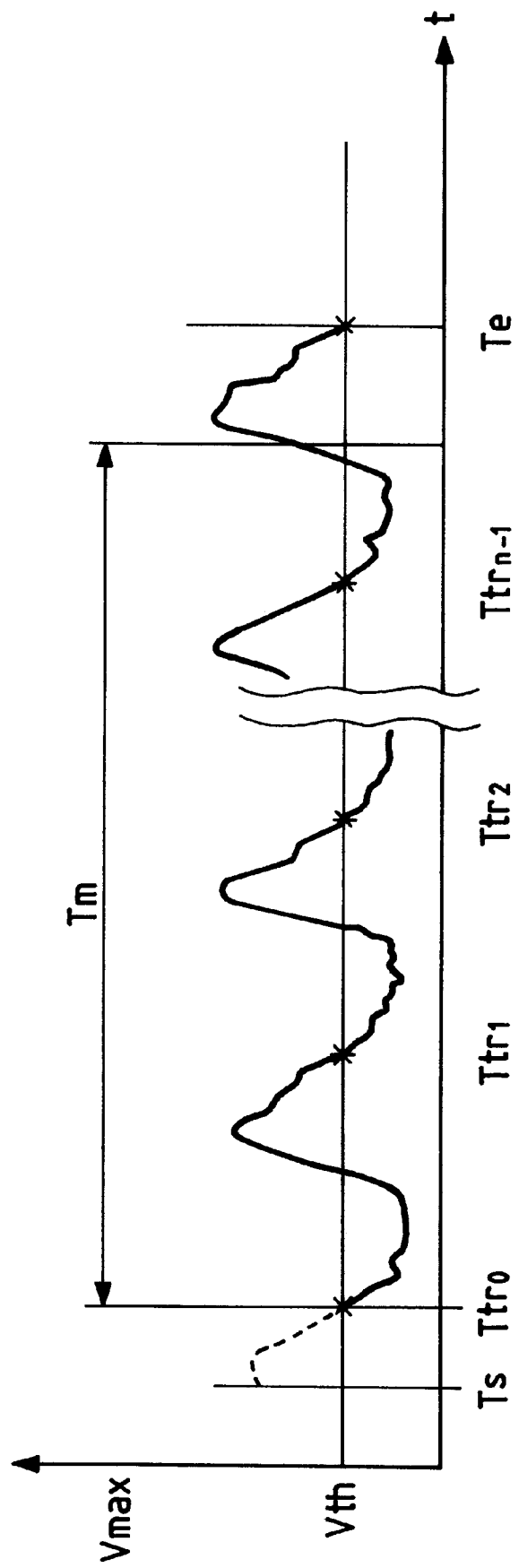
FIG. 12 is a graphical illustration of blood current velocity recording.

Whether this data is a trigger point is then judged. The trigger point can be determined by various conditions such as a minimum value and a maximum value, but herein, as shown in FIG. 12, a point below a certain threshold value Vth is defined as the trigger point.

First, the average of a points from Vmax(i−2n+1) to Vmax(i−n) is taken as V1 and further, the average of n points from Vmax(i−n+1) to Vmax(i) is taken as V2. The point Vmax(i−n+1) satisfying the condition of "V1>Vth and V2<Vth" relative to V1 and V2 is a point at which Vmax is below Vth, i.e., the trigger point.

When in the calculation of V1 and V2, the fluctuation and noise of the frequency of the blood current velocity are great, if the average number of points n is made great, the trigger point can be determined more stably. If conversely, it is judged that such fluctuation and noise are small, the value of n will be made small.

From the time when the first trigger point after the starting of measurement has been indicated has been detected (Ttr0 in FIG. 12), the pulsation frequency counter value k and the data recording time counter value t are counted up, whereafter return is made to the reading of the next output signals.

The output signals from the photo-multipliers are again read and when Vmax is calculated, the state now is a state in which the recording time counter value t ≠0 and therefore, the recording of the data and the counting-up of the recording time counter value t are effected. The display of the data is switched to a solid line as shown in FIG. 12 so as to let the operator know that the recording of the data has been started.

Thereafter, whether this measured point is the trigger point is judged as previously described, and if it is not the trigger point, a return is made to the reading of the output signals, and this operation is repeated until the next trigger point is detected.

When the measured point is judged to be the trigger point, the pulsation frequency counter value k is counted up, and a judgment as to whether a present measurement time has elapsed is effected by the use of the data recording counter value t, and if it is judged to be still within the measurement time, a return is again made to the reading of the next output signals.

The above-described operation is repeated and at a point in time at which a prescribed number of measurement recording points is exceeded and the measured point has become the trigger point, measurement and recording are terminated. That is, in FIG. 12, at a point in time at which the first trigger point Ttrn, after a predetermined recording time Tm has elapsed from the point of time of Ttr0 at which recording has been started, has been detected, recording and measurement are terminated.

The timing of termination can also be designated by the frequency of pulsation. In that case, if use is made of a program in which recording is terminated when the pulsation frequency counter value k has reached a preset frequency, data including an integer number of times of pulsation can also likewise be recorded.

Figure 13:
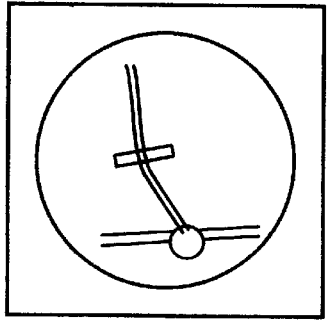
FIG. 13 is an illustration of a monitor display.
Figure 13:
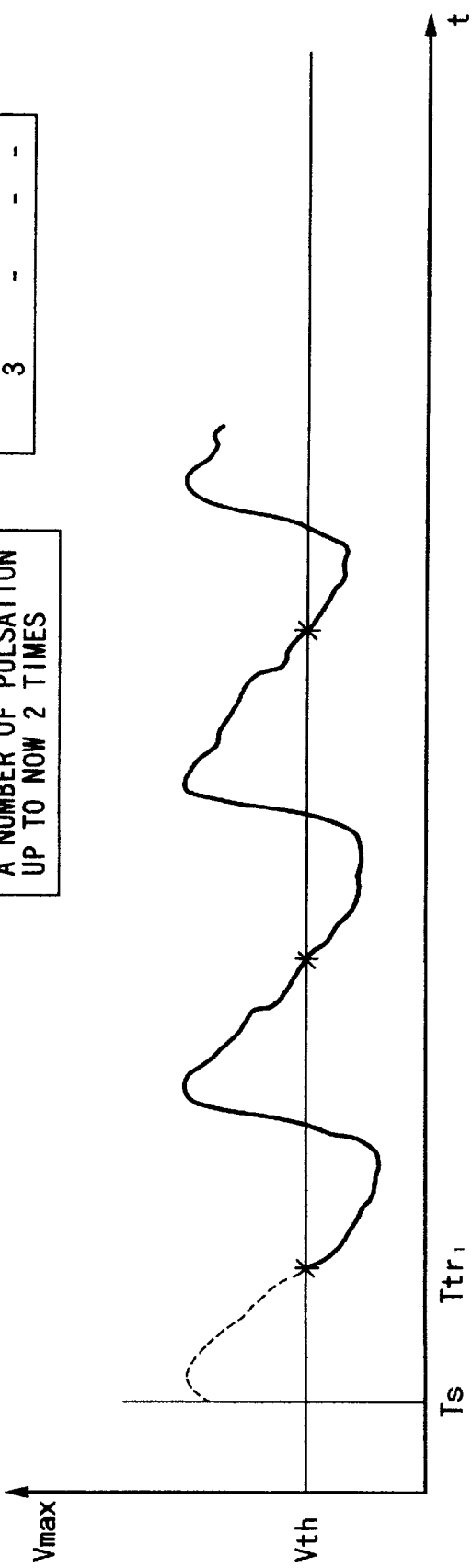

The state of display on the monitor 37 during measurement is shown in FIG. 13. In FIG. 13, a measured value plot graph (the lower side in the figure) on the monitor is displayed by a dotted line from after a point in time T0 at which the operator has depressed the measurement starting switch till the first trigger point Ttr0. It is displayed by a solid line after the trigger point Ttr0 at which recording has been started, so that the distinction, between the recorded portion of the measurement data and the portion which is not, can be easily made.

The height of the therehold value Vth of the trigger point is also displayed on the graph, and the trigger point is indicated by a mark *.

On the monitor 37, as shown in FIG. 13, other data are also displayed with the graph. As regards basic data such as patient's name, ID number and the date of measurement and measurement condition data, such as measurement time and the magnitude of the threshold value Vth, what have been inputted and set by the operator during measurement are displayed. Parameters such as the measurement time till now, the frequency of pulsation till now, the average value, the maximum value and the minimum value during each pulsation are also calculated and displayed in real time simultaneously with measurement.

The image of the fundus of the eye picked up by the CCD 36 is also displayed with the graph. The tracking beam is imprinted into the image of the fundus of the eye and thus, the retinal blood current in which region has been measured is displayed.

Figure 14:
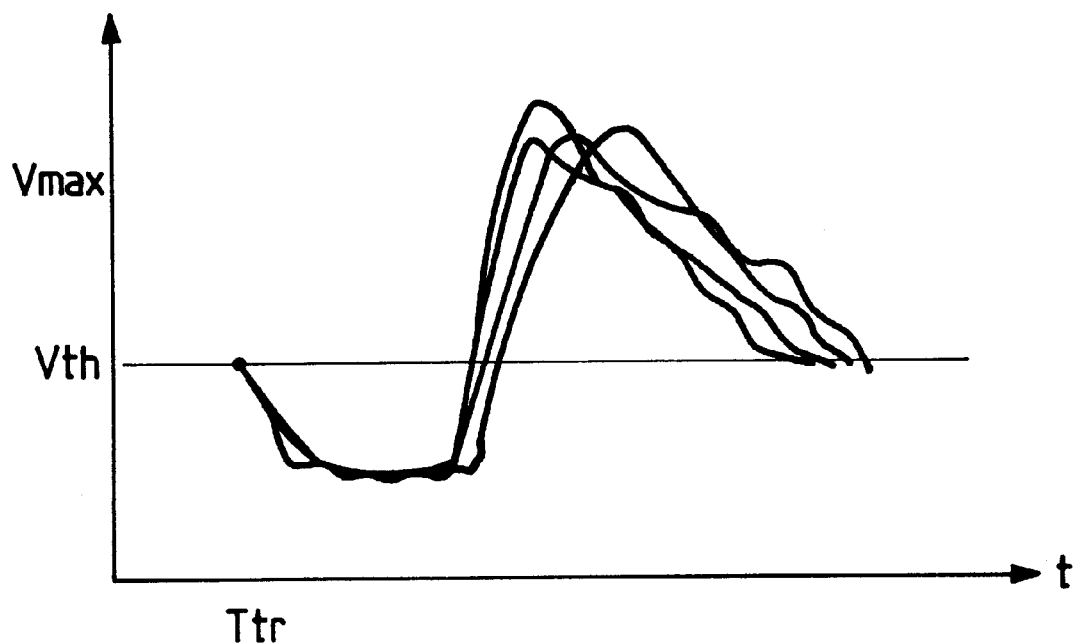
FIG. 14 is an illustration of a modification of the monitor display.

As a modification, it is also possible that during the display of the graph, as shown in FIG. 14, graphs are displayed while being superposed on one another for each pulsation with the trigger point as the starting point. If such a display method is adapted, of what a degree the irregularity of changes in the blood current velocity at each pulsation is and what the examinee's typical pulsation is like can be understood visually and intuitively.

Figure 15:
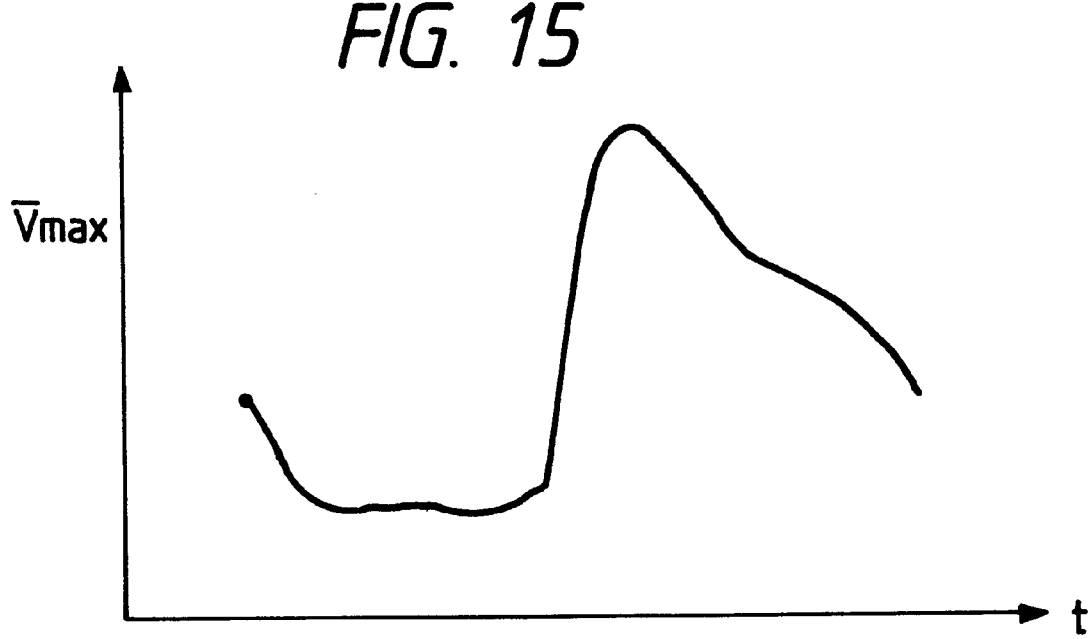
FIG. 15 is an illustration of a modification of the monitor display.

As another modification of the graphic display, it is also possible that as shown in FIG. 15, the blood current velocity from the start of recording till the present point in time is integrated for each pulsation with the trigger point as the starting point and the average thereof is displayed. In this case, the renewal of the display takes place per pulsation, but what the average pulsation is like is easy to understand.

Figure 16:
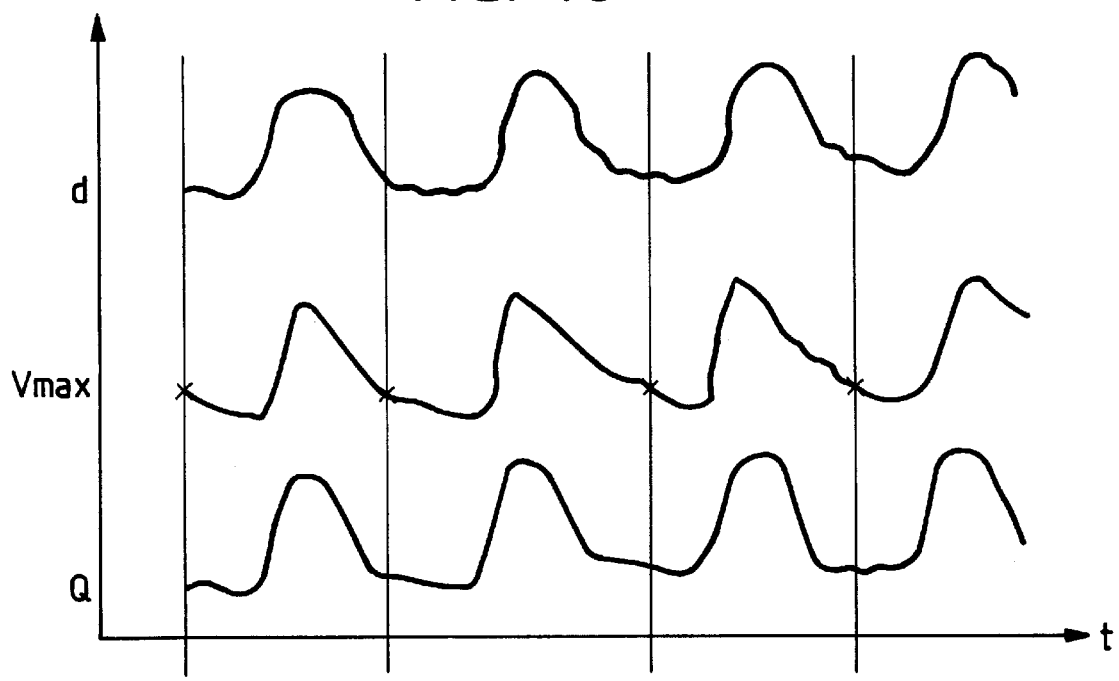
FIG. 16 is an illustration of a modification of the monitor display.

As still another modification of the graphic display, there may be adopted a form as shown in FIG. 16 wherein the blood vessel diameter d and the amount of blood current Q measured in real time are displayed with Vmax.

In the above-described embodiment the point at which the value of Vmax is below a certain threshold value Vth has been defined as the trigger point, whereas this is not restrictive, but if it is a characteristic value relative to pulsation such as the minimum value, the maximum value or a half value, the same effect can be obtained by similar means.

Figure 17:
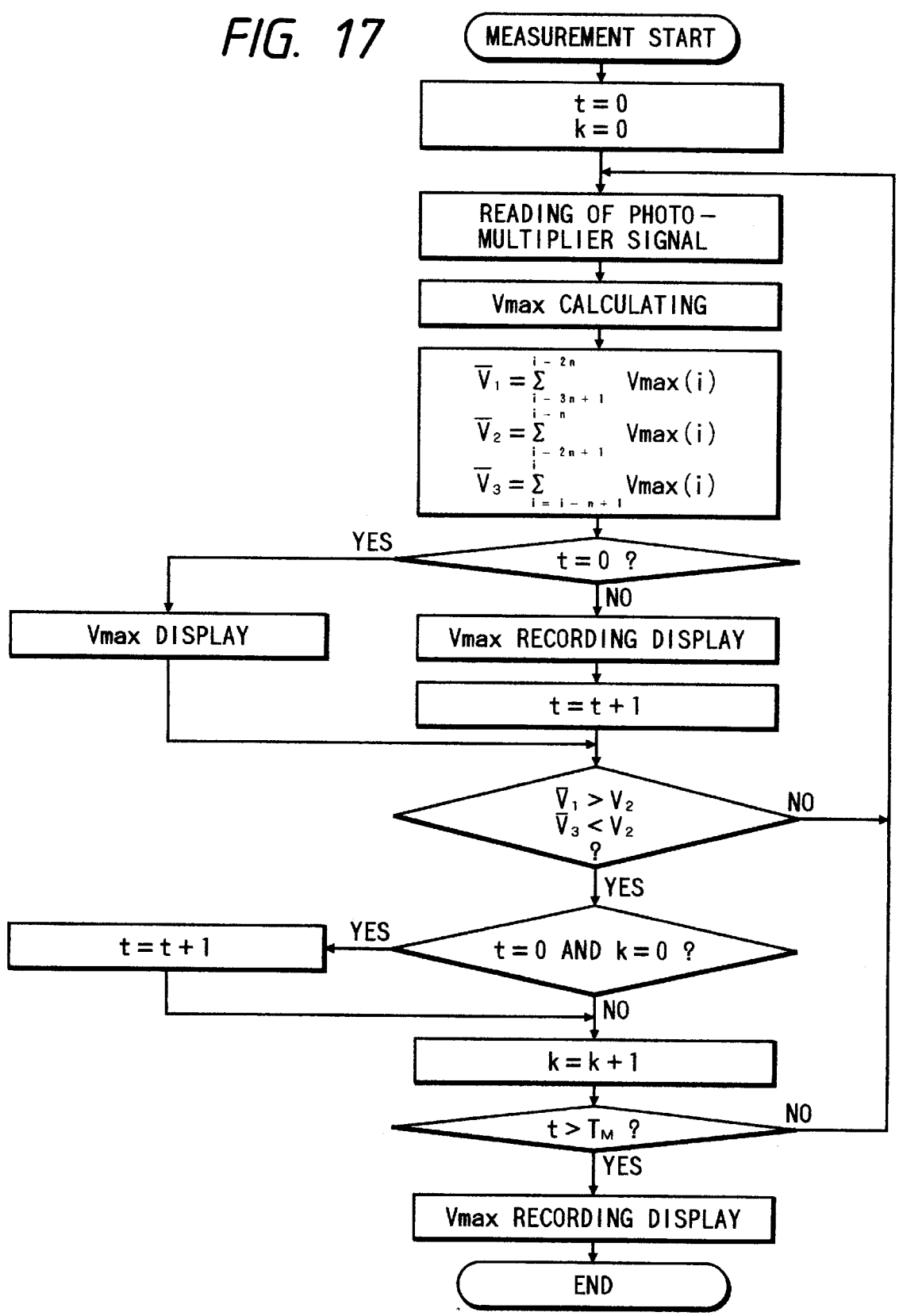
FIG. 17 is a flow chart of measurement data recording in another embodiment of the present invention.

FIG. 17 shows a flow chart of measured data recording of the controller 73 in another embodiment wherein a point at which Vmax assumes a minimum value is adopted as the trigger point for effecting the control of recording and display. Control similar to that in FIG. 11 need not be described.

In the present embodiment, the average of n points from Vmax(i−3n+1) to Vmax(i−2n) is taken as V1, the average of n points from Vmax(i−2n+1) to Vmax(i−n) is taken as V2, and further the average of n points from Vmax(i−n+1) to Vmax(i) is taken as V3, and the point Vmax(i−3n/2) or Vmax(i−(3n−1)/2) satisfying "V1>V2, V3>V2" relative to V1, V2 and V3 becomes a minimum value, and recording can be started from a measured value satisfying this condition, and the recorded data have their heads uniform at a minimum value without fail. Therefore, comparison becomes easy when a plurality of recorded data are read out and displayed.

In the above-described embodiment, the detection of the trigger point is effected from a variation in the measured value of Vmax, whereas this is not restrictive, but the measured values of the blood vessel diameter, the amount of blood current, etc. can be analyzed and the detection of the minimum value, the maximum value the half value, etc. can likewise be effected to determine the trigger point, thereby obtaining the same effect. That is, as will be understood from FIG. 16, which is a graph displaying the measured blood vessel diameter d and amount of blood current Q with Vmax, the phases of these all coincide with one another. Consequently, whichever may be used as the reference to determine the trigger point, a similar effect will be obtained.

Figure 18:
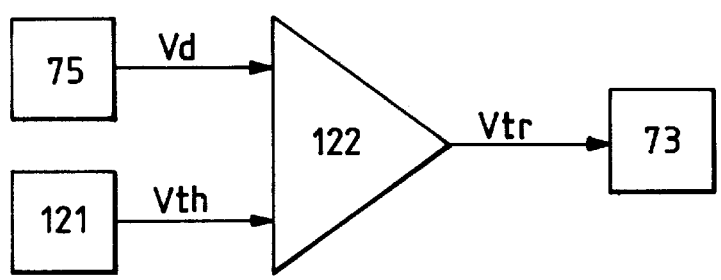
FIG. 18 is a block diagram of another example of a circuit for detecting a trigger point.

FIG. 18 is a block diagram of a trigger point detecting circuit using the blood vessel diameter. As previously described, a blood vessel diameter signal Vd representative of the blood vessel diameter is calculated by the blood vessel diameter calculating portion 75. A reference voltage Vth representative of the threshold value of the trigger point is outputted from a predetermined reference voltage generating circuit 121. Vd and Vth are compared with each other by a comparator 122, whereby a signal Vtr representative of the trigger point is produced. This signal Vtr is inputted to the controller 73 and is used for the control of the starting and termination of the recording of the data such as the blood current velocity, the control of the display, and the statistical calculation at each pulsation. This Vth can also be automatically set, for example, from the maximum value, the minimum value or the like of the blood vessel diameter within a predetermined time.

The displays shown in FIGS. 14, 15 and 16 can also be singly done, but can also be done simultaneously with other displays as shown in FIG. 13. It is also possible to make the design such that the combination of those displays can be freely set by the operator.

In the above-described embodiment, the display method and the method of calculating parameters are carried out in real time, but alternatively, the recorded data may be read into a personal computer or the like and a similar thing may be done by software. In such case, the timing of the reading of the measured data is not limited and therefore, a higher degree of calculation and display, which requires much calculation time, can be accomplished.

For example, the data of variations with time in the blood current velocity recorded by the prior-art eye fundus blood current meter are recorded independently of the phase of pulsation and therefore, the phase of the data at the head is random. So, the recorded data are read by means of a personal computer or the like and as described with reference to FIG. 11, V1 and V2 are found and trigger points below the threshold value Vth are detected. Display is started from the first trigger point, whereby the comparison with other data becomes easy. Also, statistical data of the average current speed, etc. are taken between the first and last trigger points, whereby diagnostic data having little error of phase can be obtained. Also, data such as the average, maximum and minimum blood current velocities at each pulsation can be supplied. Then, only the data between the first and last trigger points are newly recorded, whereby the data of the blood current velocities, in which the phases of pulsations are uniform, can be recorded. If at that time, data such as the otherwise recorded image of the fundus of the eye and an electrocardiogram are recorded together in the same electronic file as the blood current velocity, the information of diagnosis will be made intensive and greater efficiency of diagnosis will be achieved.

As described above, by a construction which detects the trigger point of a predetermined operation on the basis of the detection of the pulsation of the blood current in a measured area, it has become possible to effect more appropriate and accurate blood current measurement. Particularly, by a construction utilizing trigger point detection to execute the control of the starting and/or termination of the recording of measured data, the comparison with other data and the calculation of parameters such as the average current velocity, the number of pulsations and the maximum and minimum values at each pulsation have become capable of being effected accurately and appropriately. Also, by a construction which analyzes the result of the measurement of the blood current state on the fundus of the eye and detect the pulsation of the blood current in a measured area to thereby detect the trigger point of a predetermined operation, trigger point detection has become capable of being effected accurately and simply.

Also, discretely from it, by a construction which calculates the data of variations with time in the amount of blood current on the basis of the result of the measurement of variations with time in the blood current velocity and variations with time in the blood vessel diameter of a predetermined blood vessel, it has become possible to appropriately measure variations with time in the amount of blood current.

Also, discretely from it, by each of a construction which displays the data of variations with time in the measured values regarding two or more kinds of blood current states on one and the same monitor, a construction which displays the data of variations with time in the measured value regarding the blood current state and the image of the fundus of the eye to be examined on one and the same monitor, a construction which displays the measurement condition data by measuring means or a patient's data as the object of measurement and the image of the fundus of the eye to be examined on one and the same monitor, and a construction which displays the data of variations with time in the measured value regarding the blood current state and the measurement condition data by the measuring means or a patient's data as the object of measurement on one and the same monitor, it has become possible for the examiner to synthetically and appropriately judge the result of the measurement of the blood current state.

What is claimed is:

1. An apparatus for ophthalmologic examination, comprising:

an illuminating system for applying measuring light onto a measured area at least including a blood current in a fundus of an eye to be examined;

a measuring system for measuring a blood current condition of the fundus of the eye from a received light signal obtained by receiving a reflected beam of light of said measuring light on said measured area;

a pulsation detecting system for detecting pulsation of a blood current in accordance with the measurement performed by said measuring system; and a signal processing system for determining a trigger point for a predetermined operation in accordance with the detection by said pulsation detecting system.

2. The apparatus of claim 1, wherein said measuring system receives signal light created by said measuring light being scattered in said measured area by particles in a blood vessel and reference light created by said measuring light being scattered in said measured area by a blood vessel wall or its surrounding tissue as the reflected beam of light, and measures blood current velocity information of the fundus of the eye from a received light signal obtained thereby.

3. The apparatus of claim 1, wherein said measuring system has two light receiving elements for receiving the reflected beam of light on said measured area from at least two directions, and a changing member for making both of said two directions changeable relative to the blood current, and can obtain blood current velocity information of the fundus of the eye from received light signals obtained from said two light receiving elements, and can change over said two directions by use of said changing member to thereby obtain a plurality of bits of said blood current velocity information and compare said plurality of bits of blood current velocity information, and execute the changeover of control of the apparatus in accordance with said comparison.

4. The apparatus of claim 1, wherein said pulsation detecting system executes the detection of the pulsation of the blood current by the detection of the blood vessel diameter or an amount of blood current.

5. The apparatus of claim 1, further comprising a recording portion for recording the measured data by said measuring system, and wherein said recording portion utilizes said trigger point to execute control of starting and termination of the recording of the measured data as said predetermined operation.

6. The apparatus of claim 5, wherein said recording portion also records a position of the trigger point in the pulsation of said blood current with the measured data by said measuring system which vary with time.

7. The apparatus of claim 6, further comprising a monitor for displaying the measured data by said measuring system, and wherein said recording portion utilizes said trigger point to execute control of an operation of said monitor as said predetermined operation.

8. The apparatus of claim 7, wherein said monitor graphically displays the trigger point in the pulsation of said blood current with the measured data by said measuring system which vary with time.

9. The apparatus of claim 7, further comprising a recording portion for recording the measured data by said measuring system, and wherein said monitor graphically displays a recording period of said recording portion with the measured data by said measuring system which vary with time.

10. The apparatus of claim 7, wherein said monitor display variations with time in measured values at each pulsation in superposed relationship with one another with said trigger point as a starting point for starting recording of the measured data as the predetermined operation.

11. The apparatus of claim 7, wherein said monitor displays the measured data by said measuring system which vary with time, and a condition which is a reference of a determination of the trigger point.

12. The apparatus of claim 1, further comprising means for calculating statistical data of a result of a measurement by said measuring system at each pulsation.

13. The apparatus of claim 12, further comprising a monitor for displaying the measured data by said measuring system which vary with time and the statistical data.

14. The apparatus of claim 1, wherein said signal processing system analyzes a result of the measurement by said measuring system and automatically determines said trigger point.

15. An apparatus for ophthalmologic examination comprising:

an illuminating system for applying measuring light onto a measured area at least including a blood current in a fundus of an eye to be examined;

a measuring system for measuring the blood current condition of the fundus of the eye from a received light signal obtained by receiving a reflected beam of light of said measuring light on said measured area; and a signal processing system for detecting a pulsation of the blood current in said measured area in accordance with a result of a measurement by said measuring system to thereby determine a trigger point for a predetermined operation.

16. An apparatus for ophthalmologic examination, comprising:
   a blood current velocity measuring system for measuring variations with time in a blood current velocity in a predetermined blood vessel on a fundus of an eye to be examined;
   a blood vessel diameter measuring system for measuring variations with time in the blood vessel diameter of said predetermined blood vessel; and
   a signal processing system for calculating the data of variations with time in an amount of blood current in accordance with results of the measurement by said blood current velocity measuring system and said blood vessel diameter measuring system.

17. An apparatus for ophthalmologic examination, comprising:
   a measuring system for measuring a blood current condition of a fundus of an eye to be examined; and
   a monitor for displaying thereon data of variations with time in measured values of two or more kinds of predetermined parameters regarding the blood current condition which are based on a result of a measurement by said measuring system, wherein said two or more kinds of predetermined parameters include the blood current velocity, and the blood vessel diameter.

18. An apparatus for ophthalmologic examination, comprising:
   a measuring system for measuring a blood current condition of a fundus of an eye to be examined; and
   a monitor for displaying thereon data of variations with time in the measured value of a predetermined parameter regarding the blood current condition which is based on a result of the measurement by said measuring system, and an image of the fundus of the eye to be examined.

19. An apparatus for ophthalmologic examination, comprising:
   a measuring system for measuring a blood current condition of a fundus of an eye to be examined; and
   a monitor for displaying thereon data of variations with time in a measured value of a predetermined parameter regarding the blood current condition which is based on a result of the measurement by said measuring system, and the data of a measurement condition under which the measurement by said measuring system is performed by said measuring system or the data of an examinee.

20. An apparatus for ophthalmologic examination, comprising:
   illuminating means for applying measuring light onto an area to be measured at least including a blood current in a fundus of an eye;
   measuring means for measuring a blood current condition of the fundus of the eye from a received light signal obtained by receiving a reflected beam of light of said measuring light on said area to be measured;
   pulsation detection means for detecting pulsation of the blood current in said area to be measured;
   analyzing means for analyzing phase information of the pulsation of the blood current; and
   control means for controlling a predetermined operation of the apparatus on the basis of a result of an analysis by said analyzing means.

21. An apparatus for ophthalmologic examination, comprising:
   illumination applying means for applying measuring light onto a measured area at least including a blood current in a fundus of an eye;
   light receiving means for receiving reflected light of the measuring light; and generating a light-receiving output; and
   signal processing means for signal-processing the light-receiving output of said light receiving means,
   wherein said signal processing means discriminates whether a state of the blood current which is changed based on the light-receiving output of said light receiving means is satisfied with a predetermined condition; and
   wherein is said state is satisfied with the predetermined condition, then a trigger output is outputted for a predetermined operation.

22. An apparatus according to claim 21, wherein said signal processing means discriminates a state of flow velocity of the blood current.

23. An apparatus according to claim 21, wherein said signal processing means discriminates a state of blood vessel wherein the blood current is flowing or a state of the amount of blood current.

24. An apparatus according to claim 21 further comprising displaying means for displaying a state of changing of the blood current.

25. An apparatus according to claim 24, wherein said state of changing of the blood is displayed on said displaying means based on the trigger output.

26. An apparatus according to claim 24, wherein a state of flow velocity of the blood current is displayed in said displaying means.

* * * * *

UNITED STATES PATENT AND TRADEMARK OFFICE
CERTIFICATE OF CORRECTION

PATENT NO. : 5,976,096

DATED : November 2, 1999

INVENTOR(S) : Satoshi SHIMIZU et al.

It is certified that error appears in the above-identified patent and that said Letters Patent is hereby corrected as shown below:

ON THE COVER PAGE:

AT SECTION [57], IN THE ABSTRACT

Line 5, "funds" should read --fundus--.

COLUMN 1:

Line 12, "meter" should read --meter,--.

UNITED STATES PATENT AND TRADEMARK OFFICE
CERTIFICATE OF CORRECTION

PATENT NO. : 5,976,096

DATED : November 2, 1999

INVENTOR(S) : Satoshi SHIMIZU et al.

It is certified that error appears in the above-identified patent and that said Letters Patent is hereby corrected as shown below:

COLUMN 2:

Line 5, "$\Delta f\text{max}=(ks-ki)\cdot V$" should read --$\Delta f\text{max}=(\kappa s-\kappa i)\cdot v$--
Line 11, "a" should read --$\alpha$--.

COLUMN 4:

Line 59, "It's" should read --Its--.

COLUMN 5:

Line 59, "The" should read --Since the--
Line 62, "only" should read --only a--.

COLUMN 7:

Line 49, "Eat" should read --$Ea'$--.

COLUMN 8:

Line 34, "shifts $\Delta f\text{max}2$" should read --shifts $\Delta f\text{max}1$--

UNITED STATES PATENT AND TRADEMARK OFFICE
CERTIFICATE OF CORRECTION

PATENT NO. : 5,976,096

DATED : November 2, 1999

INVENTOR(S) : Satoshi SHIMIZU et al.

It is certified that error appears in the above-identified patent and that said Letters Patent is hereby corrected as shown below:

COLUMN 9:

Line 45, "$|\Delta max2'|$" should read --$|\Delta f max2'|$--.

COLUMN 10:

Line 23, "on" should red --up on--.
Line 38, "Ill" should read --111--.

COLUMN 11:

Line 45, "it" should read --in--.

COLUMN 12:

Line 65, "therehold" should read --threshold--.

COLUMN 16:

Line 40 "display" should read --displays--.

UNITED STATES PATENT AND TRADEMARK OFFICE
CERTIFICATE OF CORRECTION

PATENT NO. : 5,976,096

DATED : November 2, 1999

INVENTOR(S) : Satoshi SHIMIZU et al.

It is certified that error appears in the above-identified patent and that said Letters Patent is hereby corrected as shown below:

COLUMN 18:

Line 25, "means" should read --means, the output of which is changed based on the light-receiving output of said light receiving means,--.

Line 26, delete "which is changed".

Line 27, delete "based on the light-receiving output of said light receive".

Line 28, delete "ing means".

Signed and Sealed this

Twenty-first Day of November, 2000

Attest:

Q. TODD DICKINSON

*Attesting Officer*  *Director of Patents and Trademarks*